(12) United States Patent
Buck et al.

(10) Patent No.: US 8,136,675 B2
(45) Date of Patent: Mar. 20, 2012

(54) PERM SELECTIVE ASYMMETRIC HOLLOW FIBRE MEMBRANE FOR THE SEPARATION OF TOXIC MEDIATORS FROM BLOOD

(75) Inventors: Reinhold Buck, Alleshausen (DE); Hermann Goehl, Bisingen-Zimmern (DE)

(73) Assignee: Gambro Lundia AB, Lund (SE)

( * ) Notice: Subject to any disclaimer, the term of this patent is extended or adjusted under 35 U.S.C. 154(b) by 1130 days.

(21) Appl. No.: 10/539,409

(22) PCT Filed: Dec. 18, 2003

(86) PCT No.: PCT/SE03/01993
§ 371 (c)(1),
(2), (4) Date: Jun. 17, 2005

(87) PCT Pub. No.: WO2004/056460
PCT Pub. Date: Jul. 8, 2004

(65) Prior Publication Data
US 2006/0144782 A1     Jul. 6, 2006

(30) Foreign Application Priority Data
Dec. 20, 2002   (SE) ...................... 0203855

(51) Int. Cl.
*B01D 33/21* (2006.01)
*B01D 39/00* (2006.01)
*B01D 39/14* (2006.01)

(52) U.S. Cl. ......... 210/500.23; 210/500.27; 210/500.38; 210/500.41; 210/500.42; 210/500.43; 210/500.36

(58) Field of Classification Search ............. 210/500.23, 210/500.27, 500.38, 500.41, 500.43, 500.42, 210/500.36
See application file for complete search history.

(56) References Cited

U.S. PATENT DOCUMENTS

| | | |
|---|---|---|
| 3,423,491 A | 1/1969 | Mahon et al. |
| 3,526,588 A | 9/1970 | Baker et al. |
| 3,615,024 A | 10/1971 | Michaels |
| 4,399,035 A | 8/1983 | Nohmi et al. |
| 4,664,669 A | 5/1987 | Ohyabu et al. |
| 4,720,343 A | 1/1988 | Walch et al. |
| 4,822,489 A | 4/1989 | Nohmi et al. |

(Continued)

FOREIGN PATENT DOCUMENTS

EP    0 082 433    6/1983

(Continued)

OTHER PUBLICATIONS

Herbelin et al., Elevated circulating levels of interleukin-6 in patients with chronic renal failure, Kidney International, vol. 39, (1991), pp. 954-960.*

(Continued)

*Primary Examiner* — Krishnan S Menon
*Assistant Examiner* — Dirk Bass
(74) *Attorney, Agent, or Firm* — Barnes & Thornburg LLP

(57) ABSTRACT

The present invention relates to a permselective asymmetric hollow fibre membrane for the separation of toxic mediators from blood, comprised of at least one hydrophobic polymer and at least one hydrophilic polymer. Further, the present invention relates to a process for the preparation of such a membrane, and the use of said membrane in hemodialysis, hemodiafiltration, and hemofiltration for treatment of toxic mediator-related diseases.

17 Claims, 7 Drawing Sheets

U.S. PATENT DOCUMENTS

| | | | |
|---|---|---|---|
| 4,882,223 | A | 11/1989 | Aptel et al. |
| 4,935,141 | A * | 6/1990 | Buck et al. ............... 210/500.38 |
| 4,938,778 | A | 7/1990 | Ohyabu et al. |
| 5,009,824 | A | 4/1991 | Walch et al. |
| 5,075,003 | A | 12/1991 | Aoyagi |
| 5,340,480 | A | 8/1994 | Kawata et al. |
| 5,505,851 | A | 4/1996 | Wagener et al. |
| 5,571,418 | A * | 11/1996 | Lee et al. ...................... 210/651 |
| 5,683,584 | A | 11/1997 | Wenthold et al. |
| 5,707,522 | A | 1/1998 | Maeda et al. |
| 5,762,798 | A | 6/1998 | Wenthold et al. |
| 5,938,929 | A | 8/1999 | Shimagaki et al. |
| 6,045,899 | A | 4/2000 | Wang et al. |
| 6,565,782 | B1 | 5/2003 | Wang et al. |
| 6,802,820 | B1 * | 10/2004 | Gorsuch et al. ............. 604/6.04 |
| 6,802,971 | B2 | 10/2004 | Gorsuch et al. |
| 6,890,435 | B2 | 5/2005 | Ji et al. |
| 2004/0060866 | A1 * | 4/2004 | Radunsky et al. ............ 210/647 |
| 2004/0167237 | A1 * | 8/2004 | Kim et al. ...................... 521/50 |
| 2006/0234582 | A1 | 10/2006 | Gohl et al. |

FOREIGN PATENT DOCUMENTS

| | | |
|---|---|---|
| EP | 0168 783 A1 | 1/1986 |
| EP | 0168783 | 1/1986 |
| EP | 0 305 787 A1 | 3/1987 |
| EP | 0 305 787 | 3/1989 |
| EP | 0305787 | 3/1989 |
| EP | 0 568 045 | 11/1993 |
| EP | 0568045 | 11/1993 |
| KR | 9507322 B | 7/1995 |
| KR | 2001061733 A | 6/2001 |
| WO | WO 86/00028 | 1/1986 |
| WO | WO95/05887 | 3/1995 |
| WO | WO 9637282 | 11/1996 |
| WO | WO-01/78805 A1 | 10/2001 |
| WO | WO 2004/056459 | 7/2004 |

OTHER PUBLICATIONS

Deppisch et al., Blood material interactions at the surfaces of membranes in medical applications, 1998, 14, pp. 241-254.*
Baker, R. W., et al., "Membrane separation systems—recent developments and future directions," Williams Andrew Publishing, pp. 96-125 (1991), online version available at http://www.knovel2/Toc.jsp? BookID=312&VerticalID=O.
Combined Chemical Directionary, 2007. Triton X 100. online version available at http://ccd.chemnetbase.com/dictionarysearch.d?method=view&id=510427.
Klein, E. et al., "Transport and mMechanical properties of hemodialysis hollow fibers," Journal of Membrane Science, pp. 371-396 (1976).
International Search Report of International Application No. PCT/SE2003/001985 dated Apr. 15, 2004.
Office Action from U.S. Appl. No. 10/540,123, dated Nov. 30, 2007.
English-language translation for KR 2001-0061733 from the Korean Intellectual Property Office dated Jul. 7, 2001.
Derwent English-language Abstract for KR 2001-0061733, dated Jul. 7, 2007.
Derwent English-language Abstract for KR-9507322, dated Jul. 10, 1995.
English-language translation for KR-93-0023056, which is the priority document for KR-9507322 from the Korean Intellectual Property Office, dated Jul. 10, 1995.
esp@cenet English-language Abstract for EP0168783, dated Jan. 22, 1986.
esp@cenet English-language Abstract for WO8600028, dated Jan. 3, 1986.
U.S. Appl. No. 10/540,123, filed Jun. 20, 2005.
Esp@cenet Summary for EP 0 082 433, published on Jun. 29, 1983.
International Search Report for International Application No. PCT/SE2003/001993, dated Mar. 10, 2004.
Office Action from U.S. Appl. No. 10/540,123, dated Nov. 26, 2008.
Office Action from U.S. Appl. No. 10/540,123, dated Apr. 9, 2009.
Office Action from U.S. Appl. No. 10/540,123, dated Oct. 28, 2009.
Office Action from U.S. Appl. No. 10/540,123, dated Jul. 16, 2010.
Office Action from U.S. Appl. No. 10/540,123, dated Mar. 16, 2010.
Renaflo® II Hemofilters leaflet, Minntech Therapeutic Technologies (2007).
Communication from European Patent Office for European Patent Application No. 03 781 225.2-2113(which is a member of the same patent family as U.S. Appl. No. 10/539,409), dated Mar. 17, 2009 inviting Applicant to file observations.
Reply to EPO Communication dated Mar. 17, 2009, for European Patent Application No. 03 781 225.2-2113, dated Jun. 24, 2009 (which is a member of the same patent family as U.S. Appl. No. 10/539,409).
Summons to attend oral proceedings for European Patent Application No. 03 781 225.2-2113, dated Jan. 4, 2010 (which is a member of the same patent family as U.S. Appl. No. 10/539,409).
Written Submission in preparation for oral proceedings submitted during prosecution of European Patent Application No. 03 781 225.2-2113, dated May 4, 2010 (which is a member of the same patent family as U.S. Appl. No. 10/539,409).
Din En 1283 Hämodialysatoren, Hämodialfilter, Hämofilter, Hämokonzentratoren and dazugehörige Blutschlauchsysteme, Jun. 1996, submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
Comparison of properties between D3 (P170H) and a membrane according to the present invention (HCO 1100), submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
Auxiliary Request I, (clean copy) submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
Auxiliary Request I (marked-up copy), submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
Auxiliary Request II, (clean copy) submitted as attachment to Written Submission in preparation for oral proceedings dated May 4, 2010 during prosecution of European Patent Application No. 03 781 225.02-2113 (which is a member of the same patent family as U.S. Appl. No. 10/539,409).
Auxiliary Request II (marked-up copy), submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
International Standard ISO 8637, "Cardiovascular impants and artificial organs—Haemodialysers, haemodiafilters, haemofilters and haemoconcentrators," Second Edition, Oct. 1, 2004 submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
Morgera, S. et al. "Intermittent high permeability hemofiltration in septic patients with acute renal failure," Intensive Care Med., 29(11): 1989-1995 (2003), submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
Capannelli, G. et al. "Ultrafiltration Membranes: Characterization Membranes," Journal of Membrane Science, 15: 289-313 (1983), submitted as attachment to Written Submission in preparation for oral proceedings dated May 4, 2010 during prosecution of European Patent Application No. 03 781 225.2-2113 (which is a member of the same patent family as U.S. Appl. No. 10/539,409).
Calvo, JI et al. "Comparison of liquid-liquid displacement porosimetry and scanning electron microscopy image analysis to characterise ultrafiltration track-etched membranes," Journal of Membrane Science, 239: 189-197 (2004), submitted as attachment to Written Submission in preparation for oral proceedings dated May 4, 2010 during prosecution of European Patent Application No. 03 781 225.2-2113 (which is a member of the same patent family as U.S. Appl. No. 10/539,409).

Minutes from Oral Proceedings at European Patent Office for European Patent Application No. 03 781 225.2-2113, dated Jun. 10, 2010 (which is a member of the same patent family as U.S. Appl. No. 10/539,409).

Amended claims submitted during Oral Proceedings at European Patent Office for European Patent Application No. 03 781 225.2-2113, dated Jun. 10, 2010 (which is a member of the same patent family as U.S. Appl. No. 10/539,409).

Zusammenhang zwischen Spinntemperatur und Durchlässigkeit für verschiedene Membranrezepturen (graph to demonstrate the spinning temperature effect), submitted during Oral Proceedings at European Patent Office for European Patent Application No. 03 781 225.2-2113, dated Jun. 10, 2010 (which is a member of the same patent family as U.S. Appl. No. 10/539,409).

Communication from European Patent Office for European Patent Application No. 03 781 225.2-2113, dated Jul. 8, 2010 (which is a member of the same patent family as U.S. Appl. No. 10/539,409), informing Applicant of the European Patent Office's intention to grant a patent.

"The Cytochrome c Protein," downloaded from http://macromoleculeinsights.comicytochromec.php on Aug. 3, 2011.

"Basic Principles of Membrane Technology," 2d edition, Marcel Mulder, ed., 1996 Kluwer Academic Publishers, pp. 182-189.

Office Action from U.S. Appl. No. 10/540,123, dated Feb. 1, 2011, 12 pages.

Office Action from U.S. Appl. No. 10/540,123, dated Jul. 1, 2011, 14 pages.

Advisory Action from U.S. Appl. No. 10/540,123, dated Aug. 25, 2011, 4 pages.

* cited by examiner

IL-6 values in plasma and filtrate 30 min after initiation of high cut off filtration.

| | Interleukine-6 Sieving Coefficient | | | | |
|---|---|---|---|---|---|
| | 0,5 hr | 1 hr | 2 hr | 4 hr | 12 hr |
| High Cut-Off | 0,92±0,31 | 0,93±0,32 | 0,93±0,30 | 0,88±0,28 | 0,75±0,33 |
| 30 kD std HF | 0,03±0,05 | 0,01±0,03 | 0,01±0,02 | 0,01±0,02 | 0,00 |

PERM SELECTIVE ASYMMETRIC HOLLOW FIBRE MEMBRANE FOR THE SEPARATION OF TOXIC MEDIATORS FROM BLOOD

This application is a national stage application under 35 U.S.C. §371 of international application number PCT/SE2003/001993, filed Dec. 18, 2003, which claims the benefit of priority from Swedish application number 0203855-2, filed Dec. 20, 2002.

TECHNICAL FIELD OF THE INVENTION

The present invention relates to a permselective asymmetric hollow fibre membrane for the separation of toxic mediators from blood, comprised of at least one hydrophobic polymer and at least one hydrophilic polymer. Further, the present invention relates to a process for the preparation of such a membrane, and the use of said membrane in hemodialysis, hemodiafiltration and hemofiltration for treatment of toxic mediator related diseases.

BACKGROUND OF THE INVENTION

A significant number of patients in intensive care units die from a secondary complication known commonly as "sepsis" or "septic shock". Medical illness, trauma, complication of surgery, and any human disease state, if sufficiently injurious to the patient, may develop into systemic inflammatory response syndrome ("SIRS"), multi-organ system dysfunction syndrome ("MODS"), and multi-organ system failure ("MOSF").

The mechanism of SIRS is the excessive release of host derived inflammatory mediators, herein referred to as toxic mediators ("TM"). TM include various cytokines (tumor necrosis factor, TNF; the interleukins; interferon), various prostaglandins (PG $I_2$, $E_2$, Leukotrienes), various clotting factors (platelet activating factor, PAF), various peptidases, reactive oxygen metabolites, and various poorly understood peptides which cause organ dysfunction (myocardial depressant factor, MDF). If the inflammatory response is excessive, then injury or destruction to vital organ tissue may result in multiorgan dysfunction syndrome ("MODS"). Sepsis is the single most common cause of SIRS leading to MOSF.

Hemofiltration ("HF") was developed as a technique to control overhydration and acute renal failure in unstable patients and may use a hemofilter consisting of a cellulose derivatives or synthetic membrane (e.g., polysulfone, polyamide, etc.) fabricated as either a parallel plate or hollow fibre filtering surface. Current HF membranes, when used to treat acute renal failure associated with MOSF have been associated with incidental improvements in organ function other than the kidneys. However, these membranes remain deficient in the treatment of MOSF because their specific design characteristics prevent them from removing TM in the upper molecular weight range of recognized TM.

The pores of most conventional hemofiltration membranes allow passage of molecules up to 30,000 Daltons in water with very few membranes allowing passage of molecules up to 50,000 Daltons. The membranes used to treat renal failure were generally designed to achieve the following specific goals: (i) to permit high conductance of the aqueous phase of blood plasma water needed to permit the formation of ultrafiltrate at a fairly low transmembrane pressure (typically 20-40 mm Hg), which requires a relatively large pore size that incidentally passes molecules of up to 30,000 to 50,000 Daltons; and (ii) to avoid passage of albumin (e.g., 68,000 Daltons). Loss of albumin, and subsequently, oncotic pressure, could cause or aggravate tissue oedema and organ dysfunction (e.g., pulmonary oedema), so hemofilters are often designed to avoid this by having molecular weight exclusion limits well below the molecular weight of albumin (e.g., 68,000 Daltons).

During filtration of protein containing solutions, after only 20 min the accumulation of protein as a gel or polarization layer occurs on the membrane surface. This gel layer dramatically reduces effective pore size, reducing the filterable molecular weights by roughly 10-40%. Therefore, pore sizes selected are somewhat larger than needed, anticipating a reduction in effective size.

U.S. Pat. No. 5,571,418 discloses a novel method of continuous arteriovenous hemofiltration (CAVH) using a polysulfone or similar material, hollow fibre hemofilter with a molecular weight exclusion limit of up to 100,000 to 150,000 Daltons as therapeutic regimen for sepsis, multiple organ failure (MOF), systemic inflammatory response syndrome (SIRS) or other mediator-related diseases.

The device and process described in U.S. Pat. No. 5,571,418 generally contemplates the use of large pore hemofiltration membranes with pore sizes to provide molecular weight exclusion limits of 100,000 to 150,000 Daltons in water. With these higher molecular weight cut-offs, these membranes are designed to remove a wider range of different IM's.

EP-A-0 305 787 discloses permselective assymmetric membranes suitable for hemodialysis and a process for the manufacturing thereof. Said membrane has a special three-layer structure having high diffusive permeability, comprising a first inner layer in the form of a dense rather thin skin, having a thickness below 1 µm and a maximum pore size of about 8 nm, responsible for the sieving properties, a second layer in the form of a sponge structure, having a thickness of about 1 to 15 µm and serving as a support for said first layer and a third layer in the form of a finger structure, giving the membrane a mechanical stability and having a thickness of about 20 to 60 µm. The membrane is manufactured by presolving the hydrophobic first polymer in a solvent, presolving the hydrophilic second polymer in a solvent of preferably the same kind, mixing the two solutions, extruding the mixture through the outer ring slit of a nozzle with two concentric openings, a precipitating liquid including a part of the hydrophilic second polymer flowing through the inner openings, to obtain a coagulated membrane, which is subsequently washed and preferably dried.

SUMMARY OF THE INVENTION

The object of the present invention is to provide an improved permselective asymmetric hollow fibre membrane for the separation of toxic mediators from blood, comprised of at least one hydrophobic polymer and at least one hydrophilic polymer.

This object is achieved by a membrane, which allows passage of molecules having a molecular weight of 45 000 Daltons in presence of whole blood and having a molecular weight exclusion limit in water of about 200,000 Daltons.

A further object of the invention is to provide a process for the preparation of the membrane of the present invention.

This object is achieved by a process comprising the steps of
a) dissolving the at least one hydrophobic polymer and the at least one hydrophilic polymer in a solvent to form a polymer solution,
b) extruding the formed polymer solution through an outer ring slit of a nozzle with two concentric openings, c) extruding a centre fluid through the inner opening of the nozzle, and d) subsequently washing and preferably drying the membrane, wherein the polymer solution comprises 10-20 weight % hydrophobic polymer and 2-11 weight % hydrophilic polymer.

Yet another object of the invention is to provide a use of the membrane for treatment of toxic mediator related diseases, especially sepsis, in hemodialysis mode, hemodiafiltration mode and hemofiltration mode.

The present invention comprises HD, HDF and HF methods using a novel membrane fabricated with a pore size capable of allowing passage of molecules of about 45,000 Daltons in presence of whole blood and having an exclusion limit in water of about 200,000 Daltons. The membrane of the present invention is useful in treating human patients with SIRS-MOSF and provides for removal by filtration and/or diffusion of the entire known range of TM.

By the membrane of the invention a high selectivity is achieved, i. e. a high removal of toxic mediators having a molecular weight of up to 45,000 Dalton is achieved at the same time as a low amount of albumin, having a molecular weight of 68,000 Dalton is lost. Moreover, the risk for proteins which penetrate into the membrane structure to be absorbed in the pore structure of the membrane and thus change the permeability of the membrane, is highly reduced.

Other objects, features, advantages and preferred embodiments of the present invention will become apparent from the following detailed description when taken in conjunction with the drawings and the appended claims.

BRIEF DESCRIPTION OF THE DRAWINGS

Preferred embodiments of the present invention will now be described in more detail, reference being made to the enclosed drawings, in which.

DETAILED DESCRIPTION OF PREFERRED EMBODIMENTS

Figure 1A:
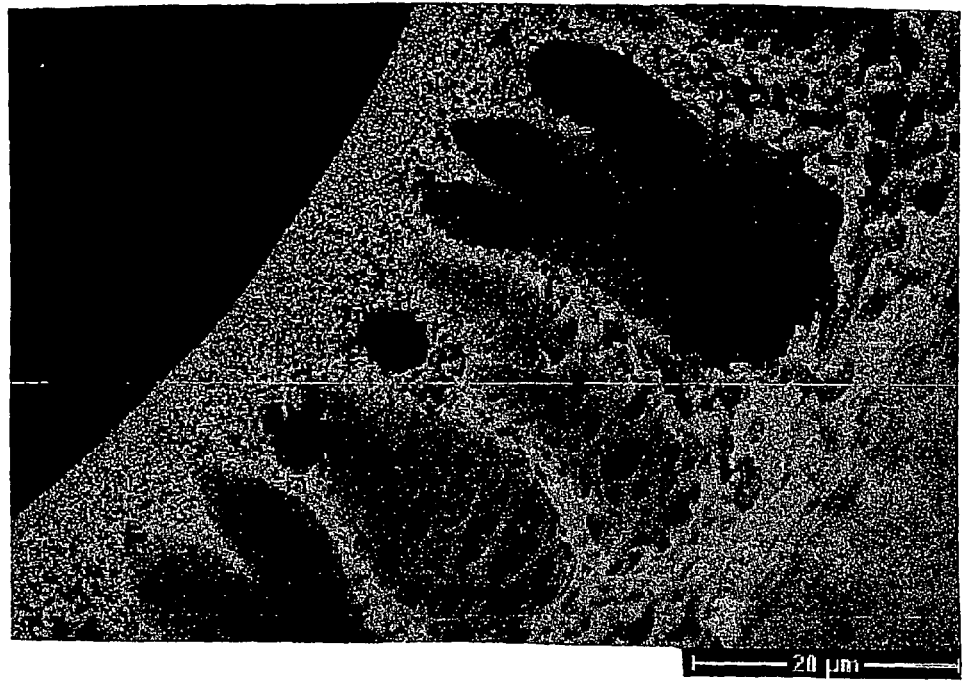
FIGS. 1a and 1b show scanning electron microscopic pictures of cross sections of the membrane structure according to a preferred embodiment of the invention.

The present invention provides a permselective asymmetric hollow fibre membrane for use in a method of treating a pathophysiological state by filtering and/or dialysing blood, comprising the steps of: withdrawing blood from a mammal; filtering and/or dialysing the blood; and returning said blood to the mammal. The methods of the present invention may use either continuous arteriovenous or continuous venovenous hemofiltration, hemodiafiltration or hemodialysis.

As used herein, the term "hemodialysis", HD, refers to a process to correct the chemical composition of blood by removing accumulated metabolic products and adding buffer in a process of diffusion through a natural or synthetic semi-permeable membrane.

As used herein, the term "hemodiafiltration", HDF, refers to a process to remove accumulated metabolic products from blood by a combination of diffusive and convective transport through a semi-permeable membrane of high-flux type; fluid is removed by ultrafiltration and the volume of filtered fluid exceeding the desired weight loss is replaced by sterile, pyrogen-free infusion solution.

As used herein, the term "hemofiltration", HF, refers to a process of filtering blood by a membrane with separation of plasma water and solutes with the ultrafiltrate, and retaines all proteins larger than effective pore size and blood cells. In hemofiltration the accumulated metabolic products are removed from the blood by the process of convective transport as a consequence of ultrafiltration through a semi-permeable membrane of high-flux type; the volume of filtered fluid exceeding the desired weight loss is replaced by sterile pyrogen-free infusion solution.

As used herein, the term "ultrafiltrate" refers to the filtered plasma water and solute and molecules (including target peptides and proteins) smaller than effective pore size.

The term "hollow fibre membrane" used throughout the application text is intended to cover everything from one single hollow fibre up to several single hollow fibres and one or more bundles of such hollow fibres, each fibre having a filtrate side and a blood side.

The term "flat sheet membrane" used throughout the application text means a micropore containing flat membrane having a filtrate side and a blood side.

As used herein, the term "Toxic Mediators", TM, refers to a heterogeneous group of chemicals synthesized and released by human tissue. TM include the inflammatory mediators of SIRS (cytokines, prostaglandins, oxygen metabolites), various clotting factors, various peptidases and various toxic peptides. The molecular weight range of known TM is 1,000-60,000.

As used herein, the term "hemofilter", refers to the filter used in hemofiltration. It is configured as either a series of parallel plates or as a bundle of hollow fibres. The blood path is from a blood inlet port, through the fibres or between the plates, then to a blood outlet port. Filtration of blood occurs at the membrane with ultrafiltrate forming on the side of the membrane opposite the blood. This ultrafiltrate accumulates inside the body of the filter contained and embodied by the filter jacket. This jacket has an ultrafiltrate drainage port.

As used herein, the term "hemodialyser", refers to the semi-permeable membrane used in hemodialysis. It is configured as either a series of parallel plates or as a bundle of hollow fibres. The blood path is from a blood inlet port, through the fibres or between the plates, then to a blood outlet port. A dialysate path is from a dialysate inlet port, outside the fibres or between the plates, the to a spent dialysate drain port. The dialysing of blood occurs at the membrane by diffusion through the membrane from the blood side to the dialysate side, and adding of buffer from the dialysate side to the blood side. The dialysate comprising necessary buffer and electrolytes.

As used herein, the term "extracorporeal circuit" refers to the system of plastic tubes attached to the hemofilter which is used clinically. The arterial line is the plastic tube which carries blood from artery or vein to the blood inlet port of the hemofilter. The venous line carries blood from the blood outlet port returning to a vein. The ultrafiltrate line carries ultrafiltrate from the ultrafiltrate drainage port on the filter jacket to a reservoir from which ultrafiltrate is discarded.

As used herein, the term "effective sieving coefficient (S)" refers to the physical property of a membrane to exclude or pass molecules of a specific molecular weight:

S=(concentration in filtrate)/(concentration in feed)

For the purposes of the present invention, the appropriate membrane allows for passage of molecules in the range of toxic mediators of up to 45,000 Daltons in the presence of whole blood/blood proteins, which means the molecular weight of a substance having a sieving coefficient (S) of 0.1-1.0 in presence of whole blood.

As used herein the term "cut off" refers to "nominal cut off" which means the molecular weight of a substance having a sieving coefficient (S) of 0.1 in water.

Figure 1B:
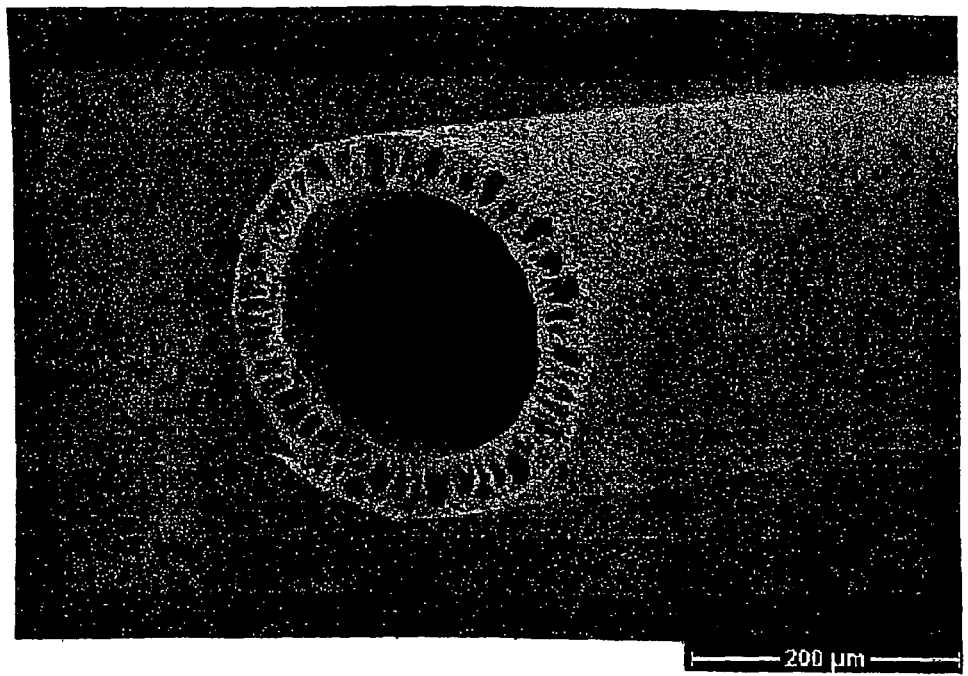
Figure 2:
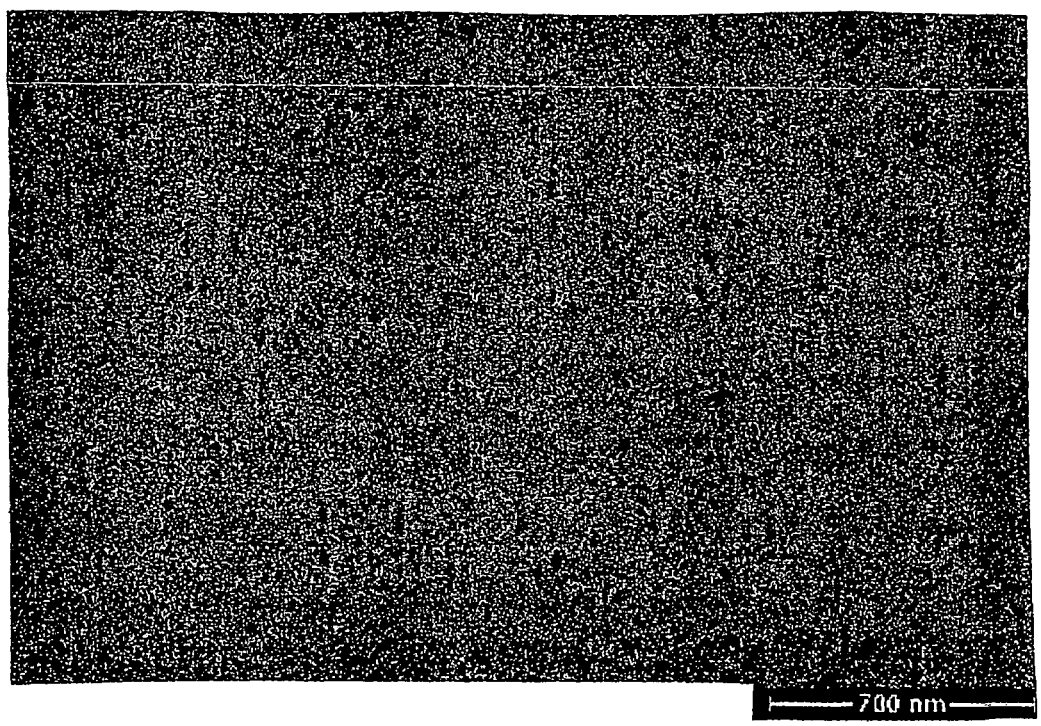
FIG. 2 shows a scanning electron microscopic picture of the inner surface of the membrane.

The membrane, in a preferred embodiment of the present invention has a unique structure, including a specific 3-layer structure with an innermost layer, i. e. a blood contacting layer, having a glomerular structure of the skin with pores having a size in the nanoscale range. In FIGS. 1a and 1b cross sections of the membrane structure according to the invention are shown, and in FIG. 2 a scanning electron microscopic picture of the inner surface of the membrane. Pore channels between glomerular polymer clusters consisting of a mixture of hydrophilic polymers and hydrophobic polymers are shown.

At least one hydrophilic polymer and at least one hydrophobic polymer are present in the membrane as domains on the surface. Preferably the hydrophobic polymer is present in an amount of 10-20 weight %, based on the weight of the membrane. The hydrophilic polymer is preferably present in an amount of 2-11 weight %, based on the weight of the membrane.

The hydrophobic polymer according to the invention may be chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), or polytetrafluorethylene (PTFE).

The hydrophilic polymer of the invention may be chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

The membrane of the invention has in a preferred embodiment at least a 3-layer asymmetric structure. In the innermost layer of the hollow fibre a separation layer is present, having a thickness of <0.5 μm and containing pore channels, having a pore size of 15-60 nm, preferably 20-40 nm. The next layer in the hollow fibre membrane is the second layer, having the form of a sponge structure and in a preferred embodiment a thickness of about 1-15 μm and serving as a support for said first layer. Then, there is the third layer, having the form of a finger structure. It provides like a framework a mechanical stability on the one hand; on the other hand it has through the high void volume a very low resistance of transport of molecules through the membrane. During the process the voids are filled with water and the water gives a lower resistance against diffusion and convection than a matrix with a sponge-filled structure having a lower void volume. Accordingly, the third layer gives the membrane a mechanical stability and has, in a preferred embodiment of the present invention, a thickness of 20 to 60 μm.

Figure 3A:
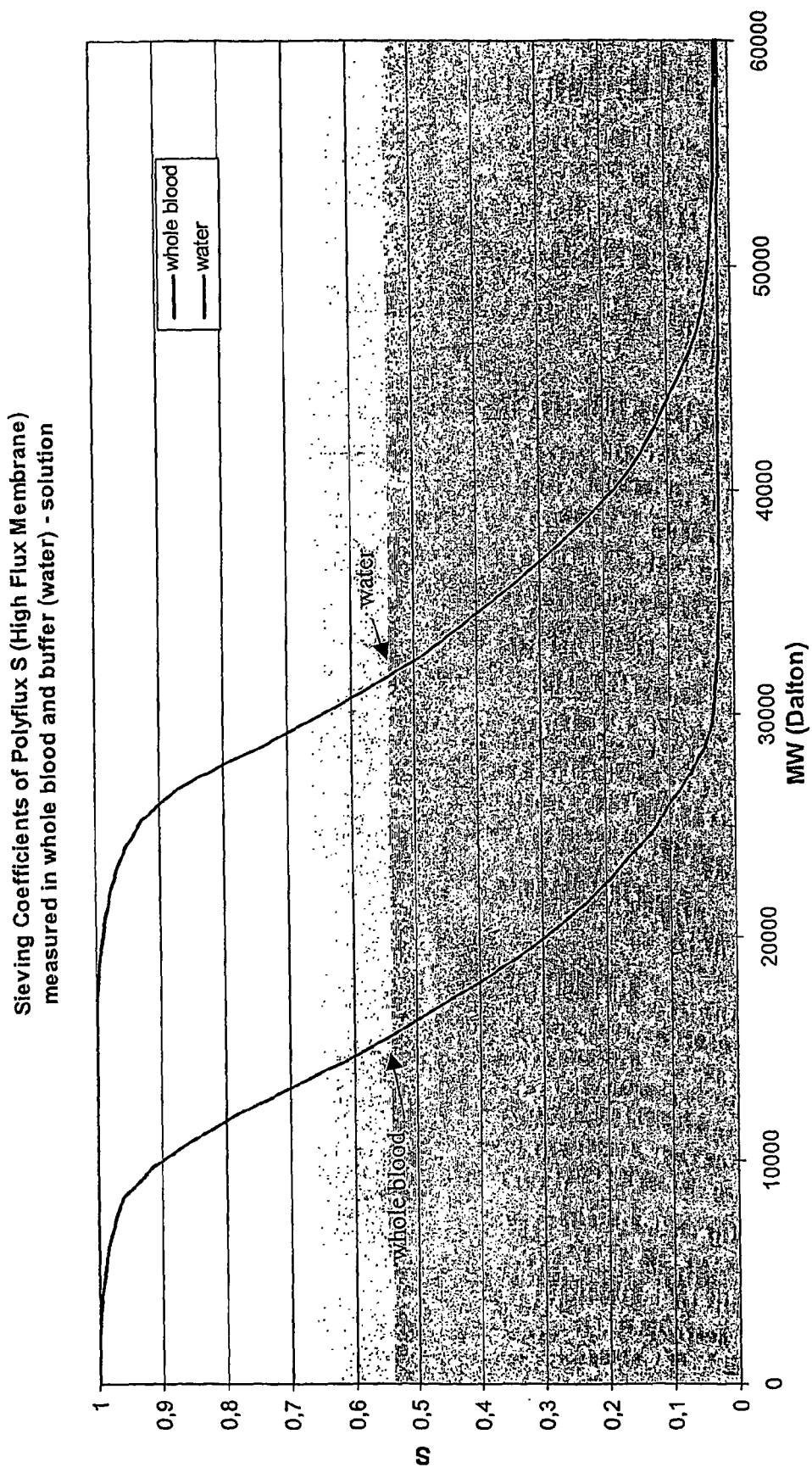
FIGS. 3a and 3b shows the sieving coefficients for two different membranes, a prior art standard "high flux membrane" and the membrane according to the invention.
Figure 3B:
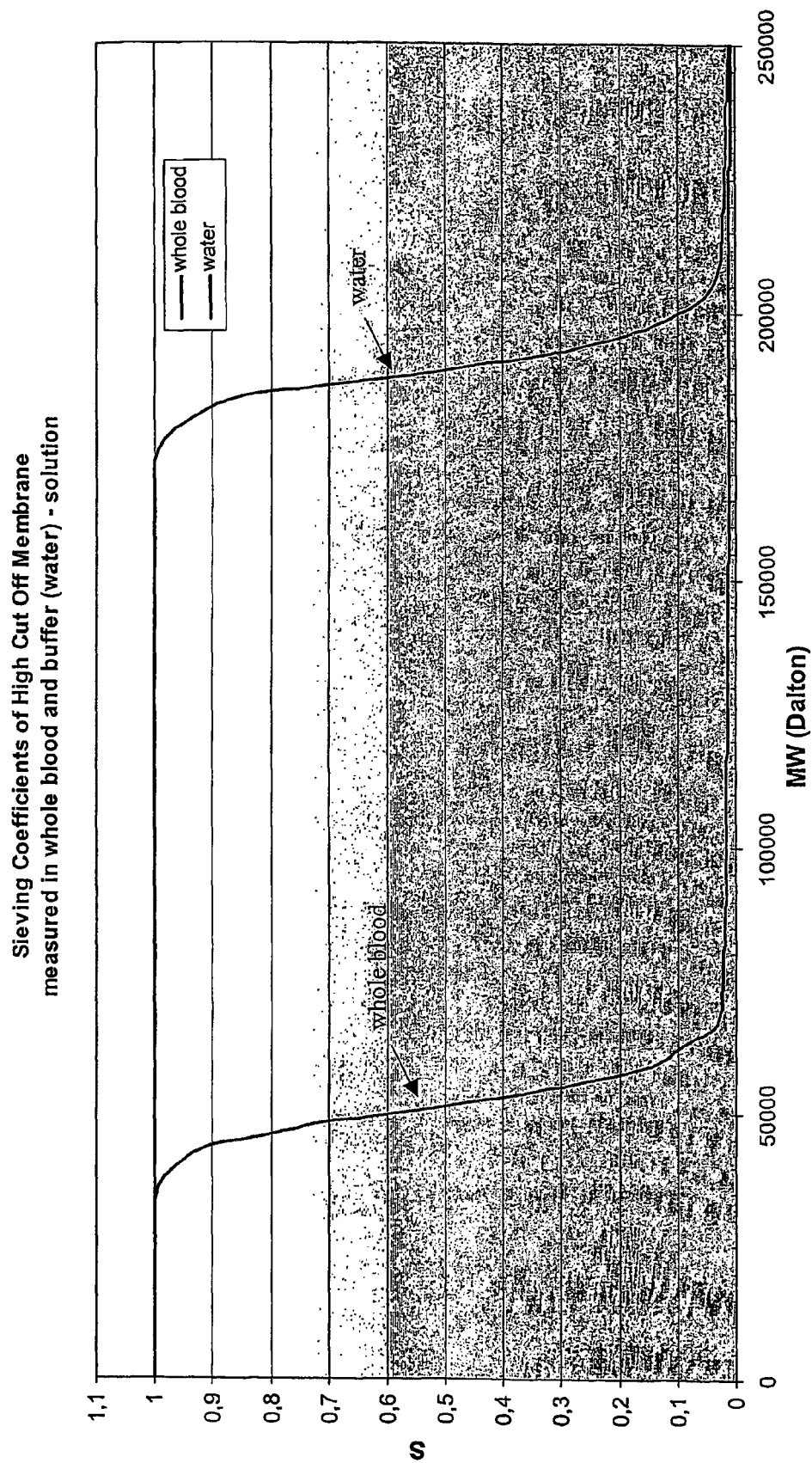
Figure 4:
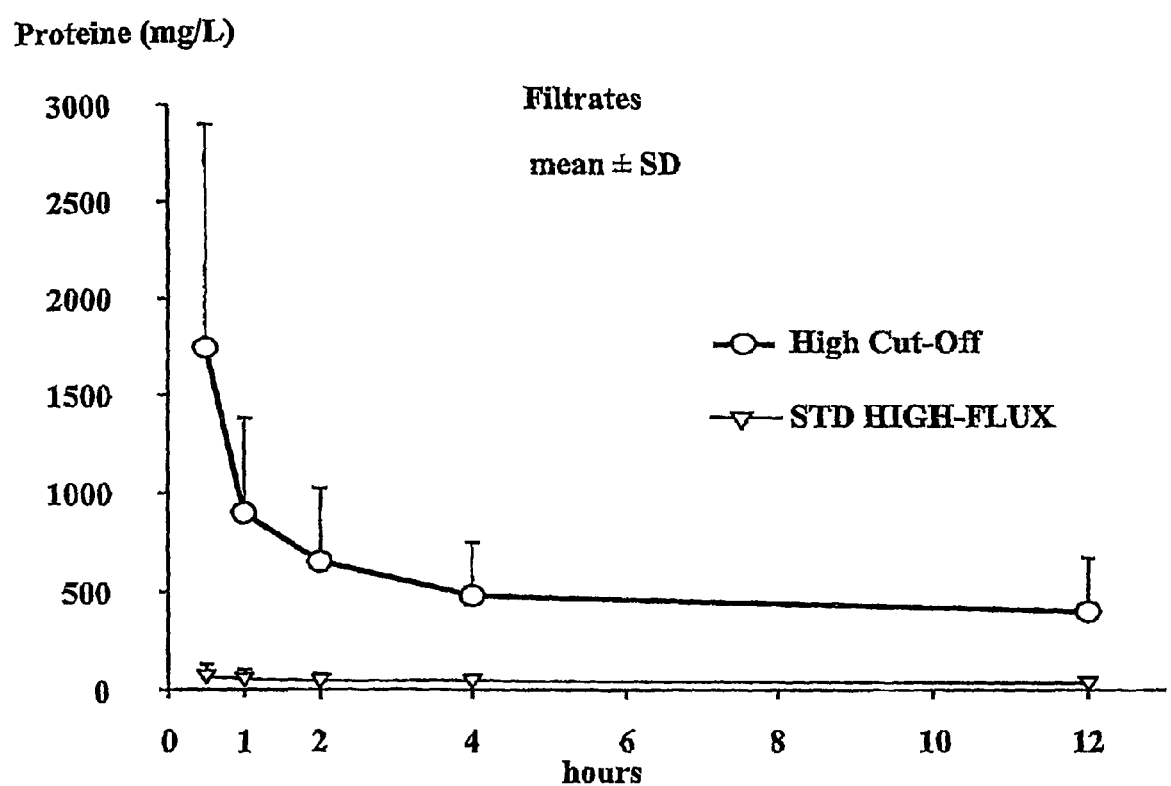
FIG. 4 shows the protein loss into the filtrate for a standard high flux membrane and for the membrane of the invention.

In FIG. 3 the sieving coefficients for two different membranes, a prior art standard "high flux membrane" and the high cut off membrane according to the invention are shown. In FIG. 4 the protein loss is illustrated. As may be seen from the figures the sieving coefficient of the membrane according to the present invention is superior to the high flux membrane and at the same time the loss of albumin is significantly lower in the membrane of the invention. According to a preferred embodiment of the invention the sieving coefficient for albumin in presence of whole blood is below 0.05.

Figure 5:
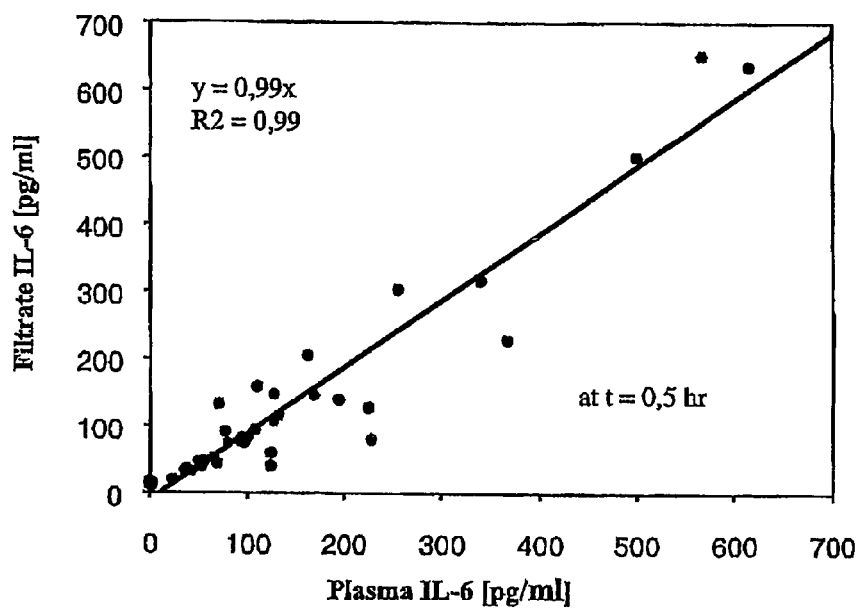
FIG. 5 shows IL-6 values in plasma and filtrate 30 min after initiation of filtration by the membrane of the invention.
Figure 6:
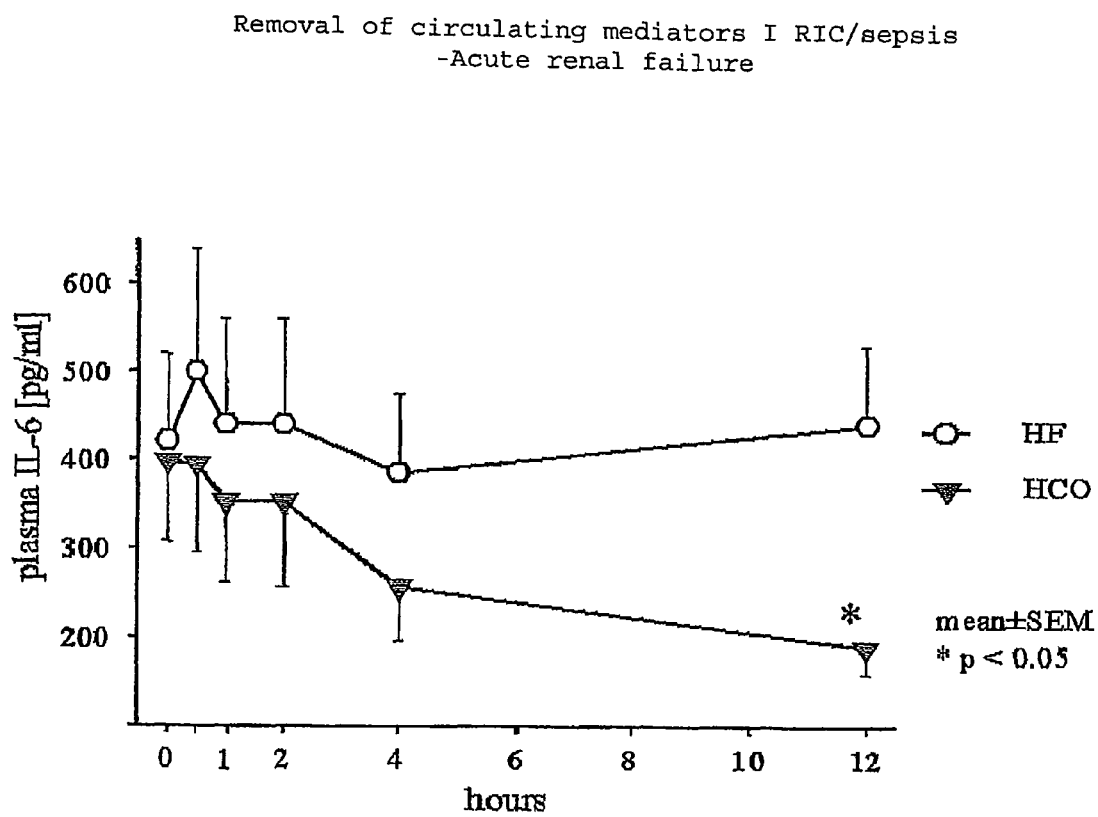
FIG. 6 shows the removal of circulating mediators in Renal Intensive Care (RIC)/sepsis for a standard high flux membrane and the membrane of the invention.

FIG. 5 and FIG. 6 shows the removal of circulating mediators in Renal Intensive Care (RIC)/sepsis. According to the invention the sieving coefficient for IL-6 in presence of whole blood is 0.9-1.0. In a preferred embodiment the membrane having the above described three-layer structure also includes a fourth layer, which is the outer surface of the hollow fibre membrane. In this preferred embodiment the outer surface has openings of pores in the range of 0.5-3 μm and the number of said pores are in the range of 10,000 to 150,000 pores/mm$^2$, preferably 20,000 to 100,000 pores/mm$^2$. This fourth layer preferably has a thickness of 1 to 10 μm.

An advantage of these embodiments is the provision of a hollow fibre membrane, which is non-sticky and is easy to handle. This results in less cracks and holes in the fibres during the manufacturing process, which in turn leads to less scrap in the manufacturing process. Another advantage is that the hollow fibre has less tendency to adhere to the hollow fibres adjacent in the bundle due to the high number of pores on the surface. Thus, the dialysate surrounding the hollow fibres during use has enhanced access to the hollow fibres since they are less inclined to adhere to each other.

This specific surface on the outside of the hollow fibre is achieved by modifying the spinning polymer solution composition only in the outer section of the hollow fibre membrane wall by penetration of water from a very specific steam/air atmosphere into the first 1-15 μm of polymer solution layer just before the precipitation from the inside arrives at this layer.

The manufacturing of the membrane according to the present invention follows a phase inversion process, wherein a polymer or a mixture of polymers is dissolved in a solvent to form a polymer solution. The solution is degased and filtered and is thereafter kept at an elevated temperature.

Subsequently, the polymer solution is extruded through a spinning nozzle (for hollow fibres) or a slit nozzle (for flat film) into a fluid bath containing a nonsolvent for the polymer. The nonsolvent replaces the solvent and thus the polymer is precipitated to an inverted solid phase.

In the present invention the polymer solution preferably is extruded through an outer ring slit of a nozzle having two concentric openings. Simultaneously a centre fluid is extruded through an inner opening of the nozzle. At the outlet of the spinning nozzle the centre fluid comes in contact with the polymer solution and at this time the precipitation is initialised. The precipitation process is an exchange of the solvent from the polymer solution with the nonsolvent of the centre fluid. Through this exchange the polymer solution inverses its phase from the fluid into a solid phase. In the solid phase there is built, by the kinetic of the solvent/nonsolvent exchange, the pore structure, i. e. asymmetry and the pore size distribution. The process works at a certain temperature which influences the viscosity of the polymer solution. According to the invention the temperature at the spinning nozzle and of the polymer solution and centre fluid is 30-80° C. The viscosity determines the kinetic of the pore forming process through the exchange of solvent with nonsolvent. Subsequently, the membrane is preferably washed and dried.

By the selection of precipitation conditions, e. g. temperature and speed, the hydrophobic and hydrophilic polymers are "frozen" in such a way that a certain amount of hydrophilic end groups are located at the surface of the pores and create hydrophilic domains. The hydrophobic polymer builds other domains. A certain amount of hydrophilic domains at the pore surface area are needed to avoid adsorption of proteins. The size of the hydrophilic domains should preferably be within the range of 20-50 nm. In order to repel albumin from the membrane surface the hydrophilic domains also need to be within a certain distance from each other. By the repulse of albumin from the membrane surface direct contact of albumin with the hydrophobic polymer is avoided and consequently the absorption of albumin.

The polymer solution preferably comprises 10-20 weight % of hydrophobic polymer and 2-11 weight % of hydrophilic polymer. The centre fluid comprises 45-60 weight % of precipitation medium, chosen from the group of water, glycerol and other alcohols, and 40-55 weight % of solvent. In other words, the centre fluid does not comprise any hydrophilic polymer.

In a preferred embodiment of the invention the polymer solution coming out through the outer slit openings is, on the outside of the precipitating fibre, exposed to a humid steam/air mixture. Preferably, the humid steam/air mixture has a temperature of at least 15° C., more preferably at least 30° C., and not more than 75° C., more preferably not more than 60° C.

Preferably, the relative humidity in the humid steam/air mixture is between 60 and 100%

Furthermore, the humid steam in the outer atmosphere surrounding the polymer solution emerging through the outer slit openings, preferably includes a solvent. The solvent content in the humid steam/air mixture is preferably between 0.5 and 5 weight % related to the water content. The effect of the solvent in the temperature controlled steam atmosphere is to control the speed of precipitation of the fibres. If less solvent is employed the outer surface will obtain a more dense surface, and if more solvent is used the outer surface will be more open structure. By controlling the amount of solvent within the temperature controlled steam atmosphere surrounding the precipitating membrane, the amount and size of the pores on the outer surface of the membrane are controlled, i. e. the size of the openings of the pores are in the range of 0.5-3 µm and the number of said pores are in the range of 10,000 to 150,000 pores/mm$^2$, preferably 20,000 to 100,000 pores/mm$^2$. The fourth layer of the membrane is preferably prepared by this method.

Before the extrusion suitable additives may be mixed into the mixture of the polymer solution. The additives are used to form a proper pore structure and optimise therewith the membrane permeability, the hydraulic and diffusive permeability and the sieving properties. The additives may be said to work as pore controller. In a preferred embodiment of the invention the polymer solution contains 0.5-7.5 weight % of a suitable additive, preferably chosen from the group comprising water, glycerol and other alcohols.

According to the invention the solvent may be chosen from the group comprising, n-methylpyrrolidon (NMP), dimethylacetamid (DMAC), dimethylsulphoxide (DMSO) dimethylformamide (DMF), butyrolactone and mixtures of said solvents.

According to a preferred embodiment of the invention, the conditions on the outside of the membrane and the combination with the polymer composition, centre fluid and temperature of the spinning nozzle, creates the optimal structure in a membrane according to the invention, i. e. four integral layers. Depending on the ratio of the components the four layers get different thickness.

It will be readily apparent to one skilled in the art that various substitutions and modifications may be made to the invention disclosed herein without departing from the scope and spirit of the invention.

The present invention will now be illustrated by way of non-limiting examples of preferred embodiments in order to further facilitate the understanding of the invention.

EXAMPLES

Example 1

A polymer solution is prepared by mixing 14 weight % of polyarylethersulfone, 0.5 weight % of polyamide, 8 weight % of PVP K30, 2 weight % of water and 75.5 weight % of NMP. A mixture of 52 weight % water and 48 weight % NMP serves as a centre and precipitation solution. The viscosity of the polymer solution, measured at a temperature of 22° C. is 4.5 Pas.

The centre and polymer solution are heated to 57° C. and pumped towards a 2-component hollow fibre spinneret. The polymer solution emerges from the spinneret through an annular slit with an outer diameter of 0.5 mm and an inner diameter of 0.35 mm. The centre solution emerges from the spinneret in the centre of the annular polymer solution tube in order to start the precipitation of the polymer solution from the inside and to determine the inner diameter of the hollow fibre.

At the same time the 2 components (polymer & centre solution) enters a space separated from the room atmosphere. This space is called spinning shaft. A mixture of steam (100° C.) and air (22° C.) is injected into the spinning shaft. The temperature in the spinning shaft is adjusted by the ratio of steam and air at 52° C. The relative humidity was adjusted to 98% and the solvent content was controlled to 4.5% by weight NMP related to water content. The length of the spinning shaft is 890 mm. By the aid of gravity and a motor-driven roller, the hollow fibre is drawn from top to bottom, from spinneret through the spinning shaft into a water bath in vertical direction. The spinning velocity is 15.0 m/min. The hollow fibre is subsequently led through a cascade of water bathes and temperatures increasing from 20 to 90° C. The wet hollow fibre membrane leaving the water rinsing bath is dried in a consecutive online drying step. After a texturising step, the hollow fibre is collected on a spinning wheel in the shape of a bundle. After introducing the bundle into a dialyser housing, it is potted with polyurethane, ends are cut, on both sides of the dialyser a header is fixed to the housing, the dialyser is rinsed with hot water and dried with air. During this last drying step, an amount of 19 g of residual water per m$^2$ effective membrane area is left on the dialyser. The filter device contains 1.1 m$^2$ effective membrane area. After labelling and packaging, the dialyser is steam-sterilized within the package in an autoclave at 121° C. for 25 min.

Example 2 (Comparative)

Compared to example no. 1, only the following was changed in the composition of the polymer solution: 16% of polyarylethersulfone, 0.5% of Polyamide, 8% of PVP K30, 0% of water and 75.5% of NMP.

The composition of the centre solution was changed to: 48% water and 52% NMP.

The polymer solution temperature was 46° C., and the spinning shaft temperature was 42° C.

Example 3 (Comparative)

Compared to example no. 1, only the following was changed in the composition of the polymer solution: 14% of polyarylethersulfone, 0.5% of polyamide, 7% of PVP K30, 3% of water, and 75.5% of NMP.

The composition of the centre solution was changed to: 60% water and 40% NMP.

The polymer solution temperature was 53° C., and spinning shaft temperature was 48° C.

Results

The resulting properties of the hollow fibre membranes according to the examples are presented in the table below.

| Example No. | LP ($10^{-4}$ cm/s/bar) | C (ml/min) | S β2M | S IL6 | S alb | Pore size (nm) |
|---|---|---|---|---|---|---|
| 1 | 218 | 181 | 0.98 | 0.95 | 0.011 | 20-40 |
| 2 | 190 | 182 | 0.99 | 0.98 | 0.146 | >100 |
| 2 | 54 | 178 | 0.81 | 0.36 | 0.002 | 10-15 |

Lp = Hydraulic permeability of water ($10^{-4}$ cm/s/bar).
C = Clearance Urea at QB = 200 ml/min, QD = 500 ml/min, UF = 0 (ml/min).
S β2M = Sieving Coefficient for β-2-Microglobulin (MW = 11,800) measured in whole blood.
S IL6 = Sieving Coefficient for Interleukin6 (MW = 26,000) measured in whole blood.
S alb = Sieving Coefficient for Albumin (MW = 68,000) measured in whole blood.

Further, it has also been shown that the membranes according to the invention could be used for diffusive high cut-off renal replacement therapy as an effective strategy to achieve good cytokine clearance while minimizing protein loss. Several treatment modes including continous venovenous hemodialysis (CVVHD), slow efficient dialysis (SLED) and intermittent hemodialysis (IHD) are conceivable.

The above-disclosed approach is an feasible method to clear cytokines much more effectively than conventional renal replacement therapies. The method does not require large amounts of sterile substitution fluids and is associated with a significant lower degree of loss of essential proteins like albumin than high cut-off hemofiltration.

The invention claimed is:

1. A permselective asymmetric hollow fibre membrane for the separation of toxic mediators from blood, comprised of at least one hydrophobic polymer and at least one hydrophilic polymer, wherein said hydrophobic polymer is selected from the group consisting of polyarylethersulfone (PAES), polypropylene (PP), polysulfone (PSU), polymethylmethacrylate (PMMA), polycarbonate (PC), polyacrylonitrile (PAN), polyamide (PA), and polytetrafluoroethylene (PTFE), and wherein said membrane comprises a separation layer and the separation layer is the inner most layer of the hollow fibre membrane, and wherein said membrane allows passage of molecules having a molecular weight of 50,000 Daltons, with a sieving coefficient of about 0.7 in the presence of whole blood, has a sieving coefficient for IL-6 in the presence of whole blood of 0.9-1.0, and has a molecular weight exclusion limit of about 200,000 Daltons in water;
wherein the membrane allows the retention of a portion of albumin in the presence of whole blood.

2. A membrane according to claim 1, wherein said at least one hydrophilic polymer and said at least one hydrophobic polymer are present in the membrane as domains on the surface,
wherein the size of the hydrophilic domains are in the range of 20-50 nm.

3. A membrane according to claim 1 wherein said at least one hydrophobic polymer is present in an amount of 50-80 weight %, based on the weight of the membrane.

4. A membrane according to claim 1 wherein said at least one hydrophilic polymer is present in an amount of 20-50 weight %, based on the weight of the membrane.

5. A membrane according to claim 1, wherein said membrane allows passage of molecules having a molecular weight of 50,000 Daltons, with a sieving coefficient of 0.7 in the presence of whole blood.

6. A membrane according to claim 1, wherein said at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

7. A membrane according to claim 1, wherein said membrane has at least a 3-layer asymmetric structure.

8. A membrane according to claim 1, wherein the separation layer has a thickness of <0.5 um.

9. A membrane according to claim 1, wherein the separation layer contains pore channels.

10. A membrane according to claim 1, wherein the pore size in the separation layer is 15-60 nm.

11. A membrane according to claim 1, wherein the sieving coefficient for albumin in the presence of whole blood is below 0.05.

12. A permselective membrane, comprised of at least one hydrophobic polymer and at least one hydrophilic polymer, wherein said membrane is provided with pores on the outer surface, wherein the average diameter of said pores is in the range of 0.5-3 μm and the number of said pores is in the range of 20,000 to 100,000 pores/mm², further wherein the structure of said membrane:
   a) allows passage of molecules having a molecular weight of up to 45,000 Daltons, with a sieving coefficient of 0.1-1.0 in the presence of whole blood;
   b) has a sieving coefficient for IL-6 of 0.9-1.0 in the presence of whole blood;
   c) has a molecular weight exclusion limit of about 200,000 Daltons in water.

13. A membrane according to claim 12, wherein said membrane has a four-layer asymmetric structure.

14. A membrane according to claim 10, wherein the pore size in the separation layer is 20-40 nm.

15. A permselective asymmetric hollow fibre membrane for the separation of toxic mediators from blood, comprised of at least one hydrophobic polymer and at least one hydrophilic polymer, wherein said membrane comprises a separation layer and the separation layer is the inner most layer of the hollow fibre membrane, and wherein said membrane allows passage of molecules having a molecular weight of 50,000 Daltons, with a sieving coefficient of 0.65 to 0.75 in the presence of whole blood, and has a molecular weight cut off of about 60,000 Daltons in the presence of whole blood;
wherein the membrane allows the retention of a portion of albumin in the presence of whole blood.

16. A membrane according to claim 15, wherein said at least one hydrophobic polymer is chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), and polytetrafluorethylene (PTFE).

17. A membrane according to claim 15, wherein said at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

* * * * *